US012624462B2

(12) United States Patent
Aniol et al.

(10) Patent No.: US 12,624,462 B2
(45) Date of Patent: May 12, 2026

(54) PROCESS FOR PREPARING PROPYLENE AND POLYPROPYLENE FROM $CO_2$

(71) Applicant: VOLKSWAGEN AKTIENGESELLSCHAFT, Wolfsburg (DE)

(72) Inventors: Armin Aniol, Braunschweig (DE); Fabian Fischer, Hannover (DE)

(73) Assignee: VOLKSWAGEN AKTIENGESELLSCHAFT (DE)

( * ) Notice: Subject to any disclaimer, the term of this patent is extended or adjusted under 35 U.S.C. 154(b) by 0 days.

(21) Appl. No.: 18/997,497

(22) PCT Filed: Jun. 23, 2023

(86) PCT No.: PCT/EP2023/067139
§ 371 (c)(1),
(2) Date: Jan. 21, 2025

(87) PCT Pub. No.: WO2024/017563
PCT Pub. Date: Jan. 25, 2024

(65) Prior Publication Data

US 2026/0028725 A1 Jan. 29, 2026

(30) Foreign Application Priority Data

Jul. 22, 2022 (DE) ..................... 10 2022 207 521.8

(51) Int. Cl.

| | |
|---|---|
| ***C07C 5/00*** | (2006.01) |
| ***C07C 1/20*** | (2006.01) |
| ***C07C 11/04*** | (2006.01) |
| ***C07C 11/06*** | (2006.01) |
| ***C07C 29/136*** | (2006.01) |
| ***C07C 29/143*** | (2006.01) |
| ***C07C 31/20*** | (2006.01) |
| ***C08F 10/06*** | (2006.01) |
| ***C25B 3/07*** | (2021.01) |
| ***C25B 3/26*** | (2021.01) |
| ***C25B 11/075*** | (2021.01) |

(52) U.S. Cl.
CPC .................. *C25B 3/07* (2021.01); *C07C 1/20* (2013.01); *C07C 11/06* (2013.01); *C07C 29/143* (2013.01); *C07C 31/205* (2013.01); *C08F 10/06* (2013.01); *C25B 3/26* (2021.01); *C25B 11/075* (2021.01)

(58) Field of Classification Search
CPC .... C25B 3/23; C25B 3/26; C07C 5/00; C07C 11/04; C07C 29/136; C08F 10/06
USPC .......... 205/462, 414, 455; 525/240; 585/638
See application file for complete search history.

(56) References Cited

U.S. PATENT DOCUMENTS

| | | | | |
|---|---|---|---|---|
| 2009/0182174 | A1 * | 7/2009 | List | C07C 253/30 568/458 |
| 2018/0127668 | A1 | 5/2018 | Masel | |
| 2020/0347502 | A1 | 11/2020 | Dismukes et al. | |

FOREIGN PATENT DOCUMENTS

| | | | |
|---|---|---|---|
| CN | 105251521 | A | 1/2016 |
| DE | 3703038 | A1 | 8/1988 |
| WO | 2021236746 | A1 | 11/2021 |

OTHER PUBLICATIONS

Horanyi et al., "Electrochemical Behaviour of 1,2-Propanediol and Methyl-Glyoxal at a Platinized Platinum Electrode in Acidic Media," Journal of Electroanalytical Chemistry and Interfacial Electrochemistry (Aug. 10, 1981), vol. 125, No. 1, pp. 105-113. (Year: 1981).*
Banerjee et al., "Mechanistic Insights into CO2 Electroreduction on Ni2P: Understanding Its Selectivity Toward Multicarbon Products," ACS Catalysis (Sep. 7, 2021), vol. 11, No. 18, pp. 11706-11715. (Year: 2021).*
Corey et al., "A Mild Procedure for the Conversion of 1, 2-Diols to Olefins," Tetrahedron Letters (Jan. 1, 1982), vol. 23, No. 19, pp. 1979-1982. (Year: 1982).*
Reid et al., "The Reduction of Some Carbonyl Compounds with Sodium Borohydride," Journal of the Chemical Society (Resumed) [1954], pp. 520-524. (Year: 1954).*
Wang et al., "Efficient and Eco-Friendly Oxidative Cleavage of C—C Bonds of 1,2-Diols to Ketones: Electrochemistry vs Thermochemistry," Organic Chemistry Frontiers (2022), vol. 9, No. 10, pp. 2664-2670. (Year: 2022).*
Maddah, "Polypropylene as a Promising Plastic: A Review," Am. J. Polym. Sci. (Jan. 2016), vol. 6, No. 1, pp. 1-11. (Year: 2016).*
Sarrami et al., "Sulphuric Acid-Catalysed Formation of Hemiacetal from Glyoxal and Ethanol," Chemical Physics Letters (May 1, 2017), vol. 675, pp. 27-34. (Year: 2017).*
Kim J et al.; Reduction of aromatic and aliphatic keto esters using sodium borohydride/MeOH at room temperature: a thorough investigation; Tetrahedron 66.23; Jun. 2010; pp. 3995-4001; Elsevier, Amsterdamn, NL.
Wang; Corey-Winter Olefination; Comprehensive Organic Name Reactions and Reagents; Sep. 15, 2010; pp. 746-749; vol. 2; Wiley, New York, NY.
Calvinho et al.; Selective CO2 reduction to C3 and C4 oxyhydrocarbons on nickel phosphides at overpotentials as low as 10 mV; Energy & Environmental Science 11.9; Nov. 2018; pp. 2550-2559; The Royal Society of Chemistry.
Larrazabal et al.; Investigation of Ethylene and Propylene Production from CO2 Reduction over Copper Nanocubes in an MEA•Type Electrolyzer; ACS Applied Materials & Interfaces 14.6; Feb. 1, 2022; pp. 7779-7787; ACS Publications.
Search Report; International Patent Application No. PCT/EP2023/067139, Feb. 14, 2024.

* cited by examiner

*Primary Examiner* — Edna Wong
(74) *Attorney, Agent, or Firm* — BARNES & THORNBURG LLP

(57) ABSTRACT

Illustrative embodiment relates to an environmentally friendly process for producing propylene and its polymer propylene from the starting material carbon dioxide $CO_2$.

15 Claims, No Drawings

PROCESS FOR PREPARING PROPYLENE AND POLYPROPYLENE FROM $CO_2$

PRIORITY CLAIM

This patent application is a U.S. National Phase of International Patent Application No. PCT/EP2023/067139, filed Jun. 23, 2023, which claims priority to German Patent Application No. 10 2022 207 521.8, filed Jul. 22, 2022, the disclosures of which are incorporated herein by reference in their entireties.

SUMMARY

Illustrative embodiments relate to an environmentally friendly process for producing propylene (i.e., propene) and its polymer polypropylene from the starting material carbon dioxide (CO2).

DETAILED DESCRIPTION

To improve the overall CO2 balance of industrial products, for example, of transportation vehicles, the use of sustainable materials is an effective lever. In this context, sustainable polymers are becoming increasingly important in large-volume industries, for example, in the transportation vehicle industry. The three most relevant raw material sources for sustainable polymers comprise renewable raw materials (bio-based approaches), recycled plastics and CO2 as the polymer raw material source.

In terms of bio-based polymers from renewable raw materials the literature already discloses a number of polymers (PLA, PHB, etc.) which make it possible to minimize the CO2 footprint over the entire product life cycle compared to the petrochemical alternative.

Increasing use is also being made of recycled plastics to minimize the CO2 footprint by a closed material circuit.

However, these two polymer classes are not suitable for use in applications with demanding requirements, since it is not possible to achieve control of the molecular weight, and thus of the physical, mechanical and chemical properties, for the bio-based approaches and for the recycled plastics due to variations in the natural raw materials and due to degradation effects in the recycling process respectively.

Calvinho et al. describe various nickel phosphides which make it possible to convert CO2 to C3-C4 compounds, such as 2,3-furandiol (C4) and the byproduct methylglyoxal (C3), in aqueous solution (Calvinho et al., Energy Environ. Sci., 2018, 11, 2550-2559).

US 2020/0 347 502 A1 likewise describes nickel phosphides for electrochemical reduction of CO2 to hydrocarbons using nickel phosphide nanoparticles.

It is possible, in turn, to produce various polymers from their associated alkenes, for example.

Suitable starting materials for these alkenes include, for example, diols which react to generate the alkene by elimination. In this regard, Lopez et al. describes the electrochemical Corey-Winter elimination reaction with trimethyl phosphite or triethyl phosphite or the known Corey-Winter reagent (Lopez et al., Beilstein H. Org. Chem. 2018, 14, 547-552).

The polymerization is effected by conventional industrial processes. Thus, for example, DE 3 703 038 A1 describes the production of branched low-pressure polyolefins having polyethene side chains, wherein polyethylene (PE) is produced from ethene using a nickel catalyst. A copolymer with short-chain α-olefins and a chromium catalyst is also disclosed.

In terms of the approach of using CO2 as the main raw material for the alkene propylene or the corresponding polymer polypropylene, no industrially applicable processes have been disclosed to date.

Accordingly, disclosed embodiments enable the synthesis of propylene and its polymer starting from CO2. The process should be employable on a large industrial scale. The yield should be as high as possible and the molecular weight should have a narrow distribution (i.e., the polydispersity should be low).

The disclosed embodiments provide a process for producing propylene (III) or polypropylene from CO2 comprising:

a) electrocatalytic reduction of the CO2 to generate methylglyoxal (I),
b) reduction of the methylglyoxal (I) from operation a) with a reducing agent to generate the corresponding 1,2-diol (II) and
c) elimination of the hydroxide groups of the 1,2-diol (II) from operation b) to generate propylene (III) according to the following reaction equation:

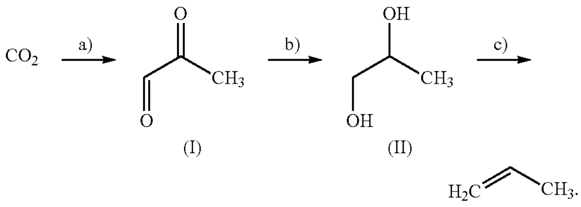

(I) (II) (III)

The compound of formula (I) is methylglyoxal, the 1,2-diol of formula (II) is 1,2-propanediol and the compound of formula (III) is propylene (propene).

The disclosed embodiments also provide for the respective use of the reagents recited in exemplary embodiments (such as catalysts, reducing agents etc.) for producing propylene or polypropylene from CO2, especially in the process disclosed.

Finally, the disclosed embodiments also provide for the use of CO2 for production of propylene and/or polypropylene, especially the use in the process disclosed.

The disclosed embodiments make it possible for the first time to produce propylene or its polymer polypropylene from CO2. The electrocatalytic reduction in operation a) may employ known catalysts. The reduction of the formed methylglyoxal in operation b) should employ a reducing agent (or else two or more different reducing agents) capable of reducing both C═O groups on the methylglyoxal to the hydroxy groups. The hydroxide groups of the resulting 1,2-diol are eliminated in operation c). Various methods are available to this end.

Finally, the disclosed embodiments also provide for the use of the polypropylene thus produced in bumpers, air filter housings, guide channels, side panels, plastic mounting supports, power units in the MEB platform, in crash absorber elements and load carriers and in electrical engineering (as transformer housings, wire and cable sheathing, insulating films, BOPP, dielectric material of plastic film capacitors and power capacitors), in the construction industry (as fittings, pipes, ventilation and air-conditioning technology in corrosive environments and in the conveying of corrosive gases) and in the textile industry (as packaging materials, hygiene products, medical products, home textiles, technical textiles) and further polypropylene products not explicitly mentioned.

It is beneficial to use the disclosed embodiments in that the process allows sustainable production of a propylene. Having regard to the CO2 footprint it is beneficial to use the disclosed embodiment to convert CO2 to useful chemical feedstocks such as propylene.

The upgraded substances produced from this propylene, such as polymers or other feedstock chemicals, also consequently have a much better CO2 balance. The CO2 footprint of the polymers over the product life cycle is negative, i.e., in the overall balance more atmospheric CO2 is bound than released.

Further utility is provided in that polypropylene polymer obtained according to the invention has substantially better properties than that made of recycled plastics, for example.

The polypropylene produced can, thus, be used in demanding applications. This is because the process makes it possible to effect control of a defined molecular weight and a narrow molecular weight distribution and thus of the physical, mechanical and chemical properties.

Operation A

In an exemplary configuration of the disclosed embodiment, it is provided that operation a) employs a nickel phosphide catalyst. $Ni_2P$ is optionally used. This is beneficial for obtaining methylglyoxal as the main product in the electrocatalytic reduction of $CO_2$.

Operation B

In an exemplary embodiment, the reduction in operation b) employs sodium borohydride ($NaBH_4$) as the reducing agent. Sodium borohydride is a strong reducing agent and is capable of reducing both carbonyl groups (C═O) of the methylglyoxal to hydroxyl groups (OH). This makes the process simpler and more cost-effective since replacement of the reducing agent is unnecessary. It is, thus, also possible to eschew intermediate purification of the monohydroxy intermediate. A significant amount of solvent is, therefore, saved. This also additionally improves the $CO_2$ balance.

The solvent in operation b) may have ethanol.

In accordance with at least one exemplary embodiment, the reduction in operation b) may be performed in two stages, the first of which is carried out in an ethanolic solution and the second of which is carried out in an acidic solution. Both exemplary embodiments have proven beneficial, especially also in the case that sodium borohydride is employed as reducing agent.

In at least one exemplary embodiment, operation b) may comprise increasing the temperature starting from −50° C. to +50° C., especially from −5° C. to +5° C., optionally from about 0° C., to room temperature.

Operation C

In accordance with at least one further exemplary embodiment, the elimination in operation c) employs a thiocarbonyl compound of formula IIa and/or a phosphorus compound selected from trimethyl phosphite, triethyl phosphite and the Corey-Hopkins reagent of formula IIb:

(IIa)

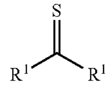

(IIb)

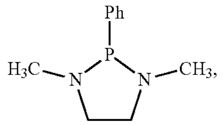

wherein $R^1$ is selected from Cl and imidazole radicals. When $R^1$=Cl the compound (IIa) is phosgene. When $R^1$=imidazole it is the Corey-Winter reagent.

Optionally, disclosed embodiments may employ both (i.e., the thiocarbonyl compound and the phosphorus compound). This is suitable for the Corey-Winter elimination as the elimination in operation c) of the process.

In accordance with at least one further exemplary configuration of the disclosed embodiments, the elimination in operation c) is carried out at 95° C. to 125° C., especially at 100° C. to 120° C., may be at 105° C. to 115° C. In these exemplary embodiments, the yield of CO2 to propylene may be high.

In a further option of this exemplary embodiment, the elimination in operation c) employs trimethyl phosphite as the phosphorus compound. This is especially yield-enhancing.

The thiocarbonyl compound may have phosgene, i.e., the thiocarbonyl compound of formula IIa where R1=Cl.

In an exemplary configuration, the two last-mentioned exemplary embodiments may be combined, i.e., the temperature in operation c) with the phosphorus compound trimethyl phosphite. This combination enables better conversion, and, thus, a reduced CO2 footprint.

In accordance with at least one exemplary configuration, the elimination in operation c) employs as the phosphorus compound the Corey-Hopkins reagent of formula IIb:

(IIb)

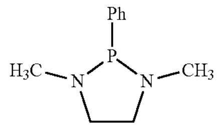

This has the technical utility of further reducing the CO2 footprint of the process.

The temperature, in this case, may be 20° C. to 80° C., especially 35° C. to 45° C., maybe 38° C. to 42° C., may be about 40° C.

The thiocarbonyl compound may have phosgene, i.e., the thiocarbonyl compound of formula IIa where R1=chlorine.

In accordance with another optional exemplary embodiment, operation c) provides that the elimination is performed by potentiostatic electrolysis at ≤−1.0 V, may be −1.9 to −1.0 V, especially at −1.7 to −1.2 V, may be at −1.5 to −1.4 V, may be at for instance, −1.45 V, against Ag/AgCl. This, too, results in better conversion and, thus, in a lower CO2 footprint on account of the low applied potential.

In accordance with another optional exemplary configuration, operation c) employs a power of 2.2 F/mol of product (±0.3 F/mol, especially ±0.15 faraday/mol).

Another exemplary configuration may employ an RVC cathode (RVC=reticulated vitreous carbon) in operation c).

These configurations may also be combined with one another.

In at least one exemplary embodiment, the CO2 eliminated in the elimination in operation c) is recycled to operation a) and reused there as starting material for the electrocatalytic reduction of CO2.

In a further optional exemplary configuration of the disclosed embodiment it is provided that the disclosure uses CO2 to produce both propylene and polypropylene. In a process for producing polypropylene from CO2 operation c) is followed by polymerization of the propylene obtained to generate polypropylene. Suitable known methods, therefor, include, for example, suspension, bulk or gas phase polymerization methods. Technical utility of this configuration is that the propylene has been upgraded and the polypropylene obtained can also be used for demanding applications since its molecular weight distribution is narrow. The molecular weight may accordingly be adjusted very precisely; more precisely than is possible in other polypropylene syntheses.

Further exemplary configurations of the disclosed embodiments derive from the other features specified in the subsidiary claims.

The various exemplary embodiments of the disclosure specified in the present application may be combined with one another unless otherwise stated in individual cases.

The disclosure will be elucidated by the exemplary embodiments specified below.

Exemplary Embodiment 1

The synthesis of polypropylene in exemplary embodiment 1 from atmospheric CO2 comprises four synthesis stages:

1.) Electrochemical reduction at $Ni_2P$ catalyst: The electrochemical reduction of the $CO_2$ is initiated by addition reaction of the carbon dioxide via the oxygen atoms with simultaneous hydride bonding to the catalytically active $Ni_2P$ surface. Protonation of these species generates formaldehyde as an intermediate. This subsequently reacts with two further formaldehyde species via C—C coupling reactions at the catalytically active electrode surface via a glycoaldehyde to generate glyceraldehyde (2,3-dihydroxypropanal). Elimination of the hydroxide group generates the reaction product of the first stage (methylglyoxal, 2-oxopropanal).

2.) Hydride exchange at sodium borohydride in EtOH: Hydride exchange is effected on the methylglyoxal using sodium borohydride and comprises addition reaction of four methylglyoxal molecules onto the boron atom via the oxygen atoms of the keto group with hydrogenation of the carbonyl carbon. This is followed by elimination of boric acid to form hydroxyacetone (1-hydroxypropan-2-one) in the acidic medium. Renewed reaction of the sodium borohydride results in formation of propylene glycol as the reaction product of the second stage.

3.) Corey-Winter elimination: The Corey-Winter elimination results in formation of propylene and is initiated by nucleophilic attack of the diol oxygens at the thiocarbonyl carbon and forms the cyclic thiocarbonate by elimination of hydrogen chloride. This is followed by nucleophilic attack of the Corey-Hopkins reagent on the sulfur atom to form a carbanion. The thiophosphoric ester is eliminated to form a cyclic carbene which forms propene as the reaction product of the third stage by $CO_2$ elimination (cyclic use as reactant in stage 1).

4.) Polymerization: The polymerization of the propene proceeds by the known industrial synthesis processes (suspension, bulk or gas phase polymerization processes).

Exemplary Embodiment 2

Also in exemplary embodiment 2 the synthesis route comprises four stages:

1. Electrochemical reduction at an $Ni_2P$ catalyst.
(exp. 11.17 kWh/kg of methylglyoxal)
2. Hydride exchange at sodium borohydride in EtOH
0° C.→RT, 65 min, (DOI: 10.15227/orgsyn.091.0185)
3. Corey-Winter elimination (DOI: 10.3762/bjoc.14.41):
→ either via trimethoxyphosphite at 111° C.
→ or via Corey-Hopkins reagent [1,3-dimethyl-2-phenyl-1,3,2-diazaphospholidine] at 40° C.
→ or via potentiostatic electrolysis at −1.45 V vs. Ag/AgCl, 2.2 F/mol, RVC cathode, 1.5 h
4. Polymerization (suspension/bulk/gas phase)

The reaction follows the following equation:

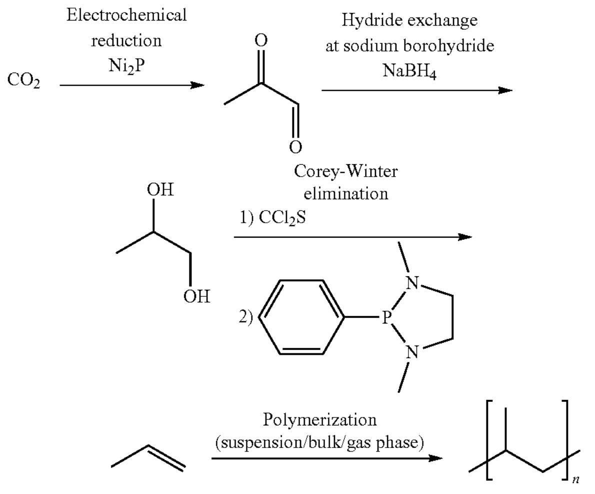

The reaction mechanism is thought to be the following:

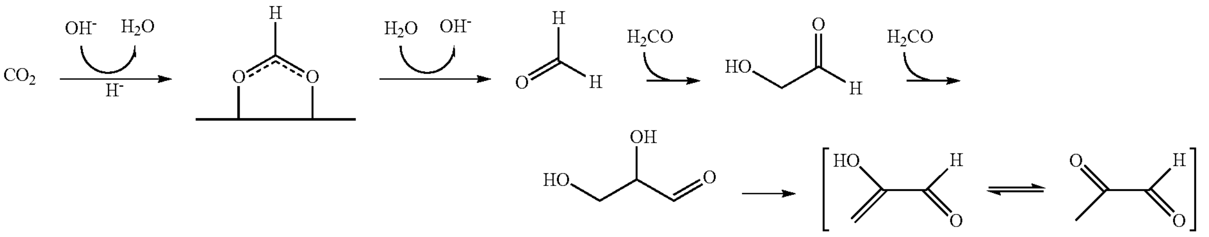

-continued

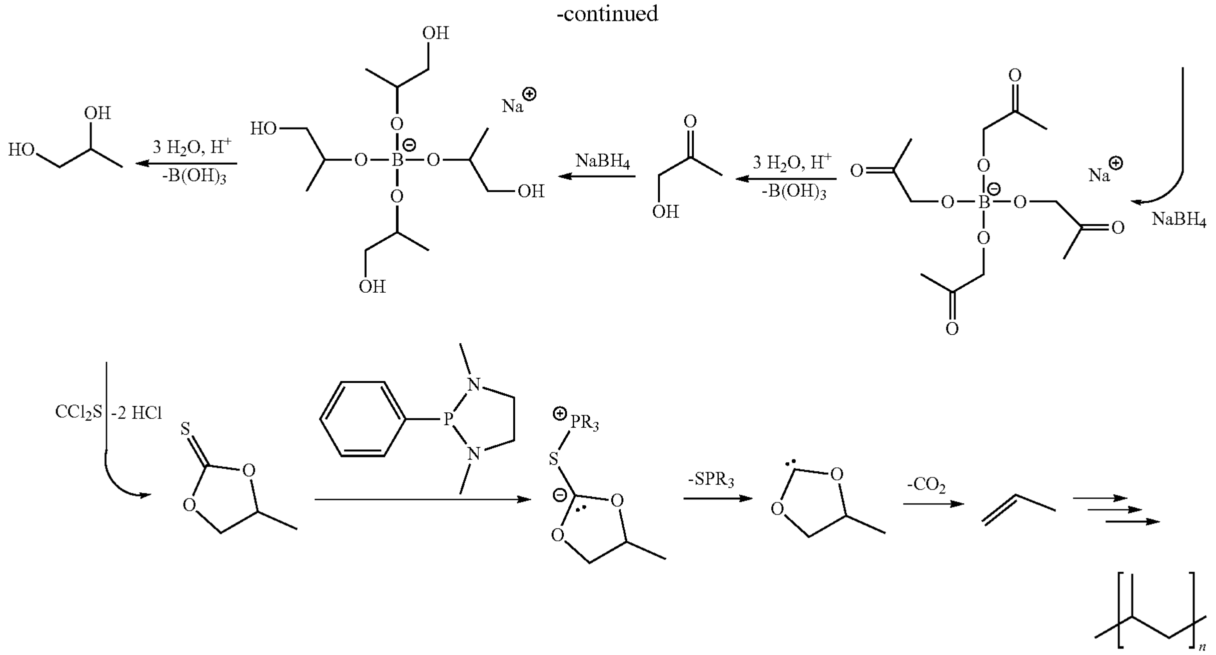

The invention claimed is:

1. A process for producing propylene (III) from $CO_2$ comprising:

electrocatalytic reduction of the $CO_2$ to generate methylglyoxal (I);

reduction of the methylglyoxal (I) in two stages, the first of which being carried out in an ethanolic solution and the second of which being carried out in an acidic solution, wherein the reduction is performed using sodium borohydride as a reducing agent to generate the corresponding 1,2-diol (II) to reduce both carbonyl groups of the methylglyoxal to hydroxyl groups; and elimination of the hydroxide groups of the 1,2-diol (II) to generate propylene (III) according to the following reaction equation:

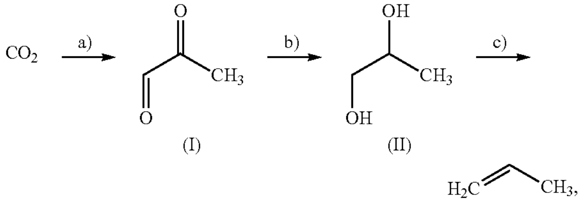

(I) (II) (III)

wherein the production of the propylene (III) from $CO_2$ is performed without replacement of the reducing agent and intermediate purification of monohydroxy intermediate thereby reducing necessary solvent and binding more atmospheric $CO_2$ than is released.

2. The process of claim 1, wherein the electrocatalytic reduction employs a nickel phosphide catalyst.

3. The process of claim 1, wherein the elimination employs a thiocarbonyl compound of formula IIa and/or a phosphorus compound selected from trimethyl phosphite, triethyl phosphite and the Corey-Hopkins reagent of formula IIb, (IIa)

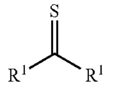

(IIb)

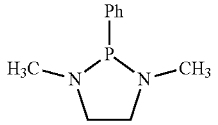

where $R^1$ is selected from Cl and imidazole radicals.

4. The process of claim 1, wherein the elimination is performed at 95° C. to 125° C.

5. The process of claim 1, wherein the elimination employs, as a phosphorus compound, the Corey-Hopkins reagent of formula IIb:

(IIb)

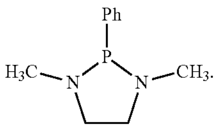

6. The process of claim 1, wherein the elimination is performed by potentiostatic electrolysis at ≤−1.0 V relative to Ag/AgCl.

7. The process of claim 1, followed by polymerization of the propylene to generate polypropylene.

8. The process of claim 7, wherein eliminated $CO_2$ is recycled for subsequent electrocatalytic reduction.

9. The process of claim 1, wherein the elimination is performed at 100° C. to 120° C.

10. The process of claim 1, wherein the elimination is performed at 105° C. to 115° C.

11. The process of claim 1, wherein the elimination is performed by potentiostatic electrolysis at −1.9 to −1.0 V relative to Ag/AgCl.

12. The process of claim 1, wherein the elimination is performed by potentiostatic electrolysis at −1.7 to −1.2 V relative to Ag/AgCl.

13. The process of claim 1, wherein the elimination is performed by potentiostatic electrolysis at −1.5 to −1.4 V relative to Ag/AgCl.

14. The process of claim 1, wherein the elimination is performed by potentiostatic electrolysis at −1.45 V, relative to Ag/AgCl.

15. A process for producing polypropylene including the process of claim 1, wherein following the operations of the propylene generation process, the polypropylene production process includes polymerization of the propylene obtained to generate polypropylene.

* * * * *